United States Patent [19]

Komatsu et al.

[11] 4,369,140
[45] Jan. 18, 1983

[54] PROCESS FOR PRODUCING HYDROANTHRAQUINONES

[75] Inventors: Tatsuyoshi Komatsu, Kamakura; Kenji Usui, Nihonbashi; Shigeaki Numata, Yokohama, all of Japan

[73] Assignee: Kawasaki Kasei Chemicals Ltd., Tokyo, Japan

[21] Appl. No.: 214,784

[22] Filed: Dec. 9, 1980

[30] Foreign Application Priority Data

Jan. 25, 1980 [JP] Japan ..................................... 55/6894

[51] Int. Cl.$^3$ .............................................. C07C 49/68
[52] U.S. Cl. .................................................. 260/369
[58] Field of Search .................... 260/369, 365, 396 R

[56] References Cited

U.S. PATENT DOCUMENTS

| 2,495,229 | 1/1950 | Pawsey | 260/369 |
| 3,870,730 | 3/1975 | Scharfe et al. | 260/369 |
| 4,155,922 | 5/1979 | Wenzel et al. | 260/369 |
| 4,176,125 | 11/1979 | Matsuura et al. | 260/369 |

Primary Examiner—Charles F. Warren
Assistant Examiner—Raymond Covington
Attorney, Agent, or Firm—Oblon, Fisher, Spivak, McClelland & Maier

[57] ABSTRACT

A hydroanthraquinone is produced from a reaction mixture obtained by the Diels-Alder reaction of naphthoquinone with a conjugated diolefin in an inert organic solvent. The reaction mixture in an inert organic solvent is oxidized with an oxidizing agent to decompose quinhydrone or quinhydrone derivative produced by said Diels-Alder reaction and the crystallized hydroanthraquinones are separated from said inert organic solvent.

6 Claims, No Drawings

PROCESS FOR PRODUCING HYDROANTHRAQUINONES

BACKGROUND OF THE INVENTION

1. Field of the Invention

The present invention relates to a process for producing hydroanthraquinones obtained by Diels-Alder reaction of naphthoquinone with 1,3-butadiene especially hydroanthraquinones including 1,4,4a,9a-tetrahydroanthraquinones.

2. Description of the Prior Art

The hydroanthraquinones including 1,4,4a,9a-tetrahydroanthraquinone (hereinafter referring to as THAQ) and 1,4-dihydroanthraquinone (hereinafter referring to as DHAQ) are important as starting materials for producing anthraquinone derivatives such as 1-aminoanthraquinone and 2-aminoanthraquinone and also anthrones such as benzanthrone. Recently, the hydroanthraquines have been considered to be important as a digesting assistant for alkaline pulp.

THAQs have been usually produced by Diels-Alder reaction of 1,3-butadiene (hereinafter referring to as BD) with naphthoquinone (1,4-naphthoquinone otherwise specified) obtained by an oxidation of naphthalene. This reaction has been usually carried out in an organic solvent.

In order to separate THAQs from the reaction mixture, it is convenient to separate crystals of THAQs precipitated by cooling the reaction mixture, by a filtration etc. It has been found that when the reaction mixture obtained by Diels-Alder reaction is cooled to crystallize the product and the resulting slurry is filtered, the filtration is remarkably difficult and the resulting hydroanthraquinones contain impurities other than derivatives having anthraquinone ring to cause lower purity.

SUMMARY OF THE INVENTION

It is an object of the present invention to provide a process for producing hydroanthraquinones including 1,4,4a,9a-tetrahydroanthraquinone as the main component which have excellent freeness in smaller solvent content in the filtration.

The foregoing and other objects of the present invention have been attained by oxidizing a reaction mixture containing hydroanthraquinones obtained by the Diels-Alder reaction of naphthoquinone with a conjugated diolefin in an inert organic solvent and separating the resulting crystals of hydroanthraquinones. The oxidation of the reaction mixture in the inert organic solvent, especially an aromatic hydrocarbon type solvent, is performed to eliminate quinhydrone which causes inferior freeness.

DETAILED DESCRIPTION OF THE PREFERRED EMBODIMENTS

It has been studied to overcome the above-mentioned disadvantages. As a result, most of impurities of the raw material and by-products are dissolved in an aromatic hydrocarbon solvents such as o-xylene which are typical inert organic solvents used in the Diels-Alder reaction. In the crystals crystallized by cooling the reaction mixture, fine crystals are included at a small ratio as well as relatively large crystals of THAQs and the fine crystals cause inferior freeness and washability of the filtered cake of the precipitated hydroanthraquinones including THAQs whereby a content of impurities in the filtered cake is increased.

The mechanism for forming the fine crystals which cause inferior freeness (filtering property) has been studied to find the fact that the material for decreasing freeness is quinhydrone as a complex of 1,4-dihydroanthrahydroquinones(hereinafter referring to as DHAHQ) and DHAQs.

In order to reduce the production of quinhydrone, quinhydrone which is contained at a small ratio in the reaction mixture obtained by Diels-Alder reaction is oxidized with an oxidizing agent such as air to convert it into DHAQs and then, hydroanthraquinones including THAQs and DHAQs are crystallized whereby fine crystal is not crystallized and moreover, the resulting crystals are remarkably larger than the crystals resulted without the oxidation, and the freeness of the resulting slurry is remarkably improved. Moreover, the solvent content of the filtered cake is remarkably low and it is remarkably easily washed whereby hydroanthraquinones including THAQs and DHAQs having remarkably high purity which has not been expected could be easily obtained by a simple washing operation. The present invention has been attained by such finding.

In the process of the present invention, hydroanthraquinones mean THAQs, DHAQs, DHAHQs and quinhydrone as a complex of DHAQs and DHAHQs or a mixture thereof. Especially, the hydroanthraquinones obtained by the present invention mean a mixture of THAQs and DHAQs as the main component, especially a mixture of THAQs as the main component which are obtained by the Diels-Alder reaction of naphthoquinone with a conjugated diolefins or derived from the product.

The Diels-Alder reaction of naphthoquinone with a conjugated diolefin especially BD is usually carried out at higher than 100° C. DHAHQs are produced as the by-product by an isomerization of the resulting THAQs. This side reaction is accelerated by a small amount of an acid or a base as well-known. DHAHQs react with naphthoquinone as the starting material or quinone type impurities in the Diels-Alder reaction to produce DHAQs. At the final stage of the reaction, the concentration of naphthoquinone as the starting material is low whereby a part of DHAHQs remains in the reaction mixture. After the completion of the Diels-Alder reaction, excess of BD is recovered. In this step, a part of THAQs as the product is isomerized to produce the by-product DHAHQs. Quinhydrone is produced by complexing the resulting DHAQs and DHAHQs during crystallization to cause inferior freeness.

On the other hand, various process for producing naphthoquinone used for the Diels-Alder reaction in the present invention, have been known. Naphthoquinone has been usually produced by an oxidation of naphthalene such as a catalytic vapor phase oxidation or a catalytic liquid phase oxidation with an oxidizing agent and it is especially produced by a catalytic vapor phase oxidation. Naphthoquinone in an industrial grade, usually contains acids such as phthalic acid and benzoic acid. Therefore, when such naphthoquinone is used as the starting material in the Diels-Alder reaction, it is difficult to prevent the production of DHAHQs, DHAQs and quinhydrone as well as THAQs as the main component.

In the process of the present invention, it is possible to effectively use an oxidizing agent which can be used for dehydrogenation of hydroanthraquinone in the oxidation of the reaction mixture obtained by the Diels-Alder reaction.

Suitable oxidizing agents include nitro compounds such as nitrobenzene and m-nitrobenzenesulfonate; quinones such as benzoquinone, naphthoquinone and dichloronaphthoquinone; and inorganic dehydrogenating agent or oxidizing agent such as ferric compounds such as ferric chloride, potassium hexacyanoferrate and ferric sulfate; thallium (III) compounds; cerium (IV) compounds; potassium permanganate; peroxides such as hydrogen peroxide; and metal oxides such as cupric oxide and magnesium oxide. Molecular oxygen such as air is also effectively used.

In accordance with the oxidation with such oxidizing agent, the oxidation is effectively performed by the reaction in the presence of the solvent by incorporating the oxidizing agent when the oxidizing agent is soluble into the reaction mixture obtained by the Diels-Alder reaction, such as nitro compounds and quinones. The oxidation can be performed by vigorously stirring the reaction mixture with an aqueous solution of the oxidizing agent to throughly contact them with the oxidizing agent which is insoluble in an organic solvent and soluble in water such as an inorganic oxidizing agent.

The oxidation can be also performed by bubbling air into the reaction mixture obtained by the Diels-Alder reaction to throughly perform the gas-liquid contact in the case of the air oxidation. The oxidation is preferably performed in the form of a solution, however it can also be performed in a form of a slurry after the crystallization of the hydroanthraquinones.

The amount of the oxidizing agent is dependent upon the amount of DHAHQs in the reaction mixture obtained by the Diels-Alder reaction and the kind of the oxidizing agent. Usually, it is more than equivalent of the stoichiometric amount required for oxidizing DHAHQs into DHAQs and less than 10 times, especially 1.0 to 1.5 times. Air can be large excess.

The reaction temperature in the oxidation is preferably in a range of 60° to 120° C. especially 70° to 90° C. in order to reduce the isomerization of THAQs and to attain the optimum reaction velocity. When the oxidation is performed in the form of a solution, the solution become transparent depending upon the performance of the oxidation and accordingly, the completion of the oxidation may be determined.

After the oxidation, the resulting solution is usually cooled to room temperature to 50° C. and the crystallized hydroanthraquinones including THAQs and DHAQs as the main components are usually separated by a conventional crystal separation such as a filtration and a centrifugal separation and are usually washed with a small amount of a solvent.

The conjugated diolefins used in the process of the present invention can be 1,3-butadiene (BD) and also substituted butadienes such as 2-methyl BD, 2-butyl BD, 2-phenyl BD, 2,3-dimethyl BD, 2-chloro BD and 2-bromo BD; and cyclopentadiene, 1,3-hexadiene, 1,3,7-octatriene and 1,3,6-octatriene.

The Diels-Alder reaction adducts obtained by using the conjugated diolefins are THAQs having the corresponding substituent such as THAQ, 2-methyl THAQ, 2-butyl THAQ, 2-phenyl THAQ, 2,3-dimethyl THAQ, 2-chloro THAQ, 2-bromo THAQ, 1,4-endomethylene THAQ and 1,4-endoethylene THAQ.

The content of DHAQs contained in the resulting hydroanthraquinone product is dependent upon the amounts of DHAHQs and DHAQs produced in the Diels-Alder reaction and in the steps before the oxidation. This can be allowable in view of the uses of the product. For examples, even though certain amount of DHAQs is contained in THAQs, the mixture can be used as the starting materials for DHAQs and benzanthrone and as a digesting assistant for alkaline pulp. If hydroanthraquinone product having high content of THAQs is required, the amount of the acid or the base in naphthoquinone as the starting material should be decreased and only the crystallized DHAQs are separated by a check filtration utilizing the difference of solubilities of THAQs and DHAQs.

The organic solvents used in the process of the present invention should be inert to naphthoquinone and the conjugated diolefins and dissolve naphthoquinone and can be distilled at lower than about 90° C. under the atmospheric pressure or a reduced pressure so as to reduce the isomerization of THAQs. Suitable solvents include aromatic hydrocarbons such as benzene, toluene and xylene; and aromatic hydrocarbon derivatives such as chlorobenzene, dichlorobenzene, trichlorobenzene and anisol; especially the aromatic hydrocarbons.

The amount of the organic solvent can be selected to be suitable for the Diels-Alder reaction and the oxidation in view of the solubilities of naphthoquinone and hydroanthraquinones especially THAQs and it can be also selected depending upon the ratio of THAQs.

After the Diels-Alder reaction, it is possible to separate the solvent to control the concentration of THAQs as desired.

The hydroanthraquinones including THAQs, DHAQs especially THAQs as the main component obtained in the process of the present invention are quite important compounds as intermediates for anthraquinone dyes. Recently, new demand as the digesting assistant for pulp has been developed and accordingly, the production of hydroanthraquinones having high purity has been required.

The process of the present invention is important to produce hydroanthraquinones having high purity especially THAQs with an industrial advantage.

In the process of the present invention, it is important to eliminate quinhydrone as the complex of DHAQs and DHAHQs by oxidizing DHAHQs to convert into DHAQs in the organic solvent, preferably an aromatic hydrocarbon or aromatic hydrocarbon derivative, especially an aromatic hydrocarbon since quinhydrone is swollen in the solvent with THAQs and DHAQs whereby the freeness of the crystals in the filtration is remarkably inferior. When quinhydrone is decomposed to convert it into DHAQs, the freeness of the crystals in the solvent is remarkably improved and the purity of the product is remarkably increased. The freeness of the crystals is quite important in the industrial operation since the production cost is remarkably decreased and the purity of the product is remarkably increased.

The present invention will be illustrated by certain examples and references in detail. In the examples, the terms "part" and "%" mean "part by weight" and "% by weight" unless otherwise specified.

EXAMPLE 1

The gaseous mixture obtained by a catalytic vapor phase oxidation of naphthalene was contacted with aqueous solution to collect the product. A solution of naphthoquinone having a concentration of 22% was obtained by extracting from the resulting slurry containing naphthoquinone with o-xylene and was washed with 0.3 parts of hot water. The resulting solution of naphthoquinone contained 0.15% of phthalic acid and 0.03% of benzoic acid based on naphthoquinone.

Into an autoclave, 100 parts of a solution obtained by concentrating the solution of naphthoquinone at a concentration of 40% and 33 parts of 1,3-butadiene and 0.1 part of t-butyl catechol were charged to carry out the Diels-Alder reaction at 120° C. for 2.5 hours. After the reaction, excess of 1,3-butadiene was distilled off to obtain a reaction mixture containing 49.4 parts of THAQ. 3.8 parts of DHAQ and 0.5 part of DHAHQ. Into the reaction mixture, 0.37 part of naphthoquinone (equimol to DHAHQ) as an oxidizing agent was added and the mixture was heated at 80° C. with stirring to react them at 80° C. for 2 hours. The resulting reaction mixture was concentrated under a reduced pressure to a concentration of 60% of hydroanthraquinones and was cooled to 40° C. and the crystallized crystals were separated by a filtration through Nutsche filter. On the Nutsche filter, the filtered cake was washed with 5 parts of o-xylene. The filtering rate was remarkably high and the solvent content was 15% based in dry. The cake was dried under a reduced pressure to obtain 32.3 parts of hydroanthraquinone.

The crystals were oxidized with air in an aqueous solution of sodium hydroxide and the purity as THAQ was calculated from the amount of anthraquinone to give 99.2%. According to an analysis by a high speed liquid chromatography, the content of THAQ was 91%.

EXAMPLE 2

In accordance with the process of Example 1 except using 41 parts of isoprene instead of butadiene, the Diels-Alder reaction was carried out. The reaction mixture was admixed with 0.87 part of nitrobenzene and the mixture was heated to 80° C. with stirring to react them for 2 hours. The resulting reaction mixture was concentrated under a reduced pressure to a concentration of 60% of hydroanthraquinones and was cooled to 40° C. and the crystallized crystals were separated by a filtration through Nutsche filter. On the Nutsche filter, the filtered cake was washed with 5 parts of o-xylene. The filtering rate was remarkably high and the solvent content was low as that of Example 1.

The cake was dried under a reduced pressure to obtain 33.5 parts of 2-methyl hydroanthraquinone including 2-methyl THAQ. The purity of crystalline 2-methyl hydroanthraquinone as 2-methyl THAQ was 99.3%.

EXAMPLE 3

The reaction mixture obtained by the Diels-Alder reaction of Example 1 was heated at 70° C. and air was bubbled with stirring at a rate of 12 parts/hour to react them for 1 hour. The resulting reaction mixture was concentrated under a reduced pressure to a concentration of 60% of hydroanthraquinones and was cooled to 40° C. and the crystallized crystals were separated by a filtration through Nutsche filter. On the Nutsche filter, the filtered cake was washed with 5 parts of o-xylene. The filtering rate was remarkably high and the solvent content was 16% based in dry. The cake was dried under a reduced pressure to obtain 32.4 parts of hydroanthraquinones. The purity of crystalline hydroanthraquinones as THAQ was 99.5%.

EXAMPLE 4

In accordance with the process of Example 1 except using monochlorobenzene instead of o-xylene, the Diels-Alder reaction was carried out. The reaction mixture was admixed with an aqueous solution containing 2 parts of ferric chloride and 20 parts of water and the mixture was heated at 80° C. with stirring to react them for 1 hour. After the reaction, the reaction mixture was kept at the same temperature for 10 minutes in standstill. The water phase was separated and the oil phase was cooled with stirring to crystallize hydroanthroquinones. The crystals were separated by a filtration through Nutsche filter. On the Nutsche filter, the filtered cake was washed with 5 parts of monochlorobenzene. The filtering rate was remarkably high and the solvent content was 17% based in dry. The cake was dried under a reduced pressure to obtain 30 parts of hydroanthraquinones. The purity of crystalline hydroanthraquinones as THAQ was 99.1%.

REFERENCE

The reaction mixture obtained by the Diels-Alder reaction of Example 1 was cooled to 40° C. without any oxidation, and the crystallized crystals were separated by a filtration through Nutsche filter. The crystals were colored blackish violet and contained fine crystals. The filtration was remarkably difficult, requiring more than 20 times the filtering time of Example 1.

Then, the cake was washed as the process of Example 1. The solvent content of the crystals was 40% based in dry. The cake was dried under a reduced pressure to obtain 32.5 parts of hydroanthraquinones in blackish violets. The purity of crystalline hydroanthraquinones as THAQ was 96.8%.

EXAMPLE 5

In accordance with the process of Example 1 except adding 0.37 part of naphthoquinone (equimol to DHAHQ) as an oxidizing agent, the mixture was heated to 80° C. with stirring to react them at 80° C. for 2 hours and cooled to 50° C. and the precipitated crystals were separated by a filtration.

The filtrate was concentrated to 60% of hydroanthraquinones under a reduced pressure and cooled to 40° C. The crystallized crystals were treated by the same process.

The crystals were oxidized with air in an aqueous solution of sodium hydroxide and the purity as THAQ was calculated from the amount of anthraquinone to give 99.1%. According to an analysis by a liquid chromatography, the content of THAQ was 98.2%.

We claim:

1. A process for production of hydroanthraquinones comprising mainly 1,4,4a,9a-tetrahydroanthraquinone by purifying crude hydroanthraquinones consisting essentially of (a) reacting naphthoquinone with a conjugated diolefin to obtain a reaction mixture containing hydroanthraquinones and quinhydrones by a Diels-Alder reaction, (b) directly oxidizing said resulting reaction mixture with an oxidizing agent in an inert organic solvent at 60° to 120° C. to decompose the quinhydrones; and (c) separating the crystallized hydroanthraquinones comprising mainly 1,4,4a,9a-tetrahydroanthraquinone substantially free from quinhydrones from said inert organic solvent.

2. The process according to claim 1 wherein said inert organic solvent is an aromatic hydrocarbon or an aromatic hydrocarbon derivative.

3. The process according to claim 1 wherein said oxidizing agent is used to oxidize dihydroanthrahydroquinone or a dihydroanthrahydroquinone derivative in said reaction mixture into the corresponding hydroanthraquinones as dihydroanthraquinone or dihydroanthraquinone derivative to decompose quinhydrone.

4. The process according to claim 1 wherein said oxidizing agent used for said oxidation is molecular oxygen, a quinone, a peroxide, a nitro compound or an inorganic oxidizing agent.

5. The process according to claim 1 wherein naphthoquinone obtained by an oxidation of naphthalene is used as the starting material.

6. The process according to claim 1 wherein said reaction mixture containing hydroanthraquinones and quinhydrones is oxidized, then 1,4-dihydroanthraquinones are crystallized and separated, and then, tetrahydroanthraquinones are crystallized and separated.

* * * * *